United States Patent [19]
Jonas et al.

[11] Patent Number: 5,434,149
[45] Date of Patent: Jul. 18, 1995

[54] THIADIAZINONES

[75] Inventors: Rochus Jonas, Darmstadt; Michael Klockow, Rossdorf; Hans-Jochen Schliep, Mühltal; Michael Wolf, Darmstadt, all of Germany

[73] Assignee: Merck Patent Gesellschaft Mit Beschrankter Haftung, Darmstadt, Germany

[21] Appl. No.: 220,657

[22] Filed: Mar. 31, 1994

[30] Foreign Application Priority Data

Apr. 1, 1993 [DE] Germany .......... 43 10 699.4

[51] Int. Cl.$^6$ .................. A61K 31/54; C07D 285/16
[52] U.S. Cl. .................. 514/222.5; 514/211; 514/212; 544/8; 540/598; 540/544
[58] Field of Search .................. 544/8; 514/222.5, 211, 514/212; 540/544, 598

[56] References Cited
U.S. PATENT DOCUMENTS
4,489,074 12/1984 Brown ........................ 544/8

*Primary Examiner*—John M. Ford
*Attorney, Agent, or Firm*—Millen, White, Zelano, & Branigan

[57] ABSTRACT

The present invention relates to thiadiazinones of the formula I

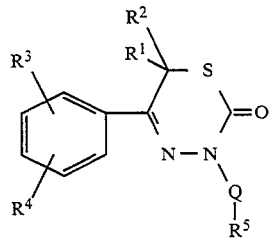

having a phosphodiesterase-inhibiting action and which are suitable for combating cardiovascular and asthmatic disorders.

14 Claims, No Drawings

THIADIAZINONES

The invention relates to thiadiazinone derivatives of the formula I

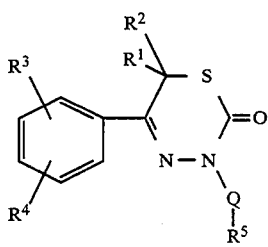

in which
R$^1$ and R$^2$ are in each case independently of one another H or A,
R$^3$ and R$^4$ are in each case independently of one another —OH, —OA, —S—A, —SO—A, —SO$_2$—A, Hal, methylenedioxy, cycloalkyloxy having 3-7 carbon atoms or O—C$_m$H$_{2m+1-k}$F$_k$,
R$^5$ is —NR$^6$R$^7$ or

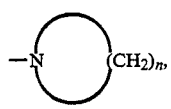

where one CH$_2$ group can also be replaced by oxygen,
R$^6$ and R$^7$ are in each case independently of one another H or A,
Q is alkylene having 1-6 carbon atoms,
A is alkyl having 1-6 carbon atoms,
Hal is F, Cl, Br or I,
m is 1, 2, 3, 4, 5 or 6,
n is 3, 4, 5 or 6
and
k is 1, 2, 3, 4, 5, 6, 7, 8, 9, 10, 11, 12 or 13, and their physiologically acceptable salts.

Thiadiazinones are known, for example, from DE 37 19 031 A1 or U.S. Pat. No. 4,916,218.

An object of the invention is discovering new compounds with valuable properties, especially those compounds which can be used for the preparation of medicaments.

It has been found that the compounds of the formula I possess valuable pharmacological properties and, in addition, are well tolerated.

In particular, they exhibit phosphodiesterase inhibition and, e.g., can be employed for the treatment of asthmatic disorders. The antiasthmatic action can be determined, for example, by the method of T. Olsson, Acta allergologica 26, (1971) 438–447. Furthermore, the compounds exhibit a cerebroprotective action and have antidepressive and antiinflammatory properties.

They can be employed for the treatment of memory disorders, are positively inotropic and have a vasodilatory effect. The substances therefore promote blood circulation.

The vasodilatory and the cardiac actions can be determined, for example, in narcoticized or conscious dogs, cats, monkeys or minipigs, and the positively inotropic action can also be demonstrated on isolated heart preparations (e.g. atrium, papillary muscle or perfused whole heart) of the rat, guinea-pig, cat or dog, for example in accordance with methods as described in Arzneimittelforschung, volume 31 (I) No. 1a (1981), pages 141 to 170, or by Schlieb et al. in 9th International Congress of Pharmacol., London, Abstracts of papers 9P.

In addition the substances possess antiallergic properties.

The compounds can therefore be used as pharmaceutically active substances in human and veterinary medicine. They can also be employed as intermediates for the preparation of further pharmaceutically active substances.

Accordingly the invention relates to the compounds of the formula I and to a process for their preparation, characterized in that a compound of the formula II

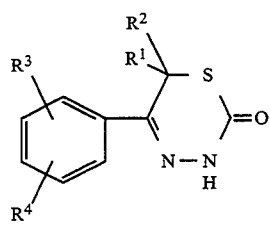

in which R$^1$, R$^2$, R$^3$ and R$^4$ have the meanings given is reacted with a compound of the formula III $$R^5\text{-Q-X} \qquad III$$

in which
R$^5$ and Q have the meanings given and
X is Cl, Br, OH or a reactive, esterified OH group,
or in that a compound of the formula IV

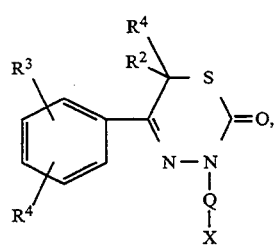

in which
R$^1$, R$^2$, R$^3$, R$^4$,
Q and X possess the meanings already given, is reacted with an amine of the formula V $$HNR^6R^7 \qquad V$$

in which
R$^6$ and R$^7$ have the meanings already given or with an amine of the formula VI

where one CH$_2$ group can also be replaced by O and in which
n possesses the meaning already given, or in that a compound which corresponds to the formula I but which possesses, instead of R$^5$, a primary or a secondary amino group is alkylated in a conventional manner, and/or in that optionally a compound which corresponds to the formula I but which contains, instead of $R^3$ and/or $R^4$, one or two free OH groups, is reacted with a compound of the formula $R^3$-X or $R^4$-X in which $R^3$, $R^4$ and X have the meanings given, and/or a base of the formula I is converted into one of its salts by treatment with an acid.

Below and above the radicals $R^1$, $R^2$, $R^3$, $R^4$, $R^5$, $R^6$, $R^7$, Q and X and the pamperers m, n and k have the meanings given for the formulae I, II, III, IV, V and VI, unless expressly stated otherwise.

In the formulae alkyl is preferably unbranched, preferably has 1, 2, 3 or 4 carbon atoms and is preferably methyl, is further preferably ethyl or propyl, and is also preferably isopropyl, butyl, isobutyl, sec-butyl or tert-butyl, but also is n-pentyl or isopentyl.

Alkoxy is preferably unbranched, preferably has 1, 2 or 3 carbon atoms and is preferably methoxy, is further preferably ethoxy or propoxy and is also, for example, isopropoxy, butoxy, isobutoxy, sec-butoxy, tertbutoxy, pentyloxy or isopentyloxy.

Alkylene is preferably unbranched and is preferably methylene or burylens, particularly preferably ethylene or propylene.

Of the radicals $R^1$ and $R^2$, one is preferably H while the other is preferably propyl or butyl, but particularly preferably ethyl or methyl.

The radicals $R^3$ and $R^4$ may be identical or different and are preferably in the 3 or 4 position of the phenyl ring. They are independently of one another, for example, hydroxyl, —S—$CH_3$, —SO—$CH_3$, —$SO_2CH_3$, F, Cl, Br or I or together are methylenedioxy. However, they are particularly preferably methoxy, ethoxy, propoxy or else are fluoro-, difluoro-, trifluoromethoxy, 1-fluoro-, 2-fluoro-, 1,2-difluoro-, 2,2-difluoro-, 1,2,2-trifluoro- or 2,2,2-trifluoroethoxy.

The radical $R^5$ is preferably methylamino, dimethylamino, ethylamino, methylethylamino, diethylamino or else pyrrolidino piperidino or morpholino, while m and k are preferably in each case 1, 2 or 3 and n is preferably 4 or 5, where one $CH_2$ group can be replaced by O.

The invention relates in particular to those compounds of the formula I in which at least one of the abovementioned radicals has one of the preferred meanings given above. Some preferred groups of compounds can be expressed by the following subformulae Ia to If, which correspond to the formula I and in which the radicals which are not defined more closely have the meaning given for formula I, but in which in Ia $R^3$ and $R^4$ are in the 3 and 4 positions, respectively, of the phenyl ring and
$R^1$ is H,
$R^2$ is H or alkyl, and
$R^3$ is OA;
in Ib $R^3$ and $R^4$ are in the 3 and 4 positions, respectively, of the phenyl ring and
$R^1$ is H,
$R^2$ is methyl or ethyl, and
$R^3$ and $R^4$ are each OA;
in Ic $R^3$ and $R^4$ are in the 3 and 4 positions, respectively, of the phenyl ring and
$R^1$ is H,
$R^2$ is methyl or ethyl,
$R^3$ is OA, and
$R^4$ is mono-, di- or trifluoroalkoxy;

in Id $R^3$ and $R^4$ are in the 3 and 4 positions, respectively, of the phenyl ring and
$R^1$ is H,
$R^2$ is methyl or ethyl,
$R^3$ is mono-, di- or trifluoroalkoxy, and
$R^4$ is OA;
in Ie $R^3$ and $R^4$ are in the 3 and 4 positions, respectively, of the phenyl ring and
$R^1$ is H,
$R^2$ is methyl or ethyl,
$R^3$ and $R^4$ are in each case independently of one another OA or mono-, di- or trifluoroalkoxy and
$R^5$-Q is 3-dimethylaminopropyl, 2-dimethylaminoethyl, 3-methylaminopropyl, 1,2-methylaminoethyl, 3-ethylaminopropyl or 2-ethylaminoethyl;
in If $R^3$ and $R^4$ are in the 3 and 4 positions, respectively, of the phenyl ring and
$R^1$ is H,
$R^2$ is methyl or ethyl,
$R^3$ and $R^4$ are in each case independently of one another OA or mono-, di- or trifluoroalkoxy and
$R^5$ -Q is pyrrolidinoethyl, pyrrolidinopropyl, piperidinoethyl, dinoethyl, piperidinopropyl, morpholinoethyl or morpholinopropyl.

The compounds of the formula I are otherwise prepared by methods which are known per se, as described in the literature (for example in the standard works such as Houben-Weyl, Methoden der Organischen Chemie [Methods of Organic Chemistry], Georg-Thieme-Verlag, Stuttgart), specifically under reaction conditions which are known and suitable for the stated reactions. In this context use can also be made of variants which are known per se and are not mentioned in more detail here.

In the compounds of the formula II $R^1$, $R^2$, $R^3$ and $R^4$ have the meanings given, especially the preferred meanings given.

In the compounds of the formula III $R^5$-Q is preferably methylamino-, dimethylamino-, ethylamino-, diethylamino- or ethylmethylaminopropyl or -ethyl, or is pyrrolidino-, piperidino- or morpholinoethyl or -propyl, while X is Cl, Br, OH or a reactive, esterified OH group. If X is a reactive, esterified OH group, then it is preferably alkylsulfonyloxy having 1-6 carbon atoms, for example methanesulfonyloxy, or arylsulfonyloxy having 6-10 carbon atoms, for example benzene-, p-toluene- or 1-or 2-naphthalenesulfonyloxy.

If desired, the starting substances can also be formed in situ, so that they are not isolated from the reaction mixture but instead immediately reacted further to give the compounds of the formula I. Alternatively it is possible to carry out the reaction in steps, and further intermediates can be isolated.

Some of the starting substances of the formulae II and III are known. Where they are not known they can be prepared by methods which are known per se.

Thiadiazinones of the formula II and their preparation are described in, for example, German Patent Application P 4134893 or U.S. Pat. No. 5,276,027.

Compounds of the formula III can be prepared by, for example, reacting suitable dihaloalkanes with the corresponding primary or secondary amines, for example, as described in J. March, Adv. Org. Chem., 3rd Ed., J. Wiley & Sons (1985). It is also possible, starting from appropriate aminoalkenes, to prepare the functional groups X by anti -Markovnikov addition of HX onto the double bond (X=halogen). Moreover, it is possible to start from the corresponding amino alcohols and to esterify them by means of reactions which are known per se, so that, for example, reactive compounds having alkylsulfonyloxy or arylsulfonyloxy groups, for example the corresponding mesylates or tosylates, are formed.

Specifically, the reaction of the thiadiazinones of the formula II with the compounds of the formula III is carried out in the presence or absence of an inert solvent at temperatures of between about −20° and about +150°, preferably between 20° and 100° C. Examples of suitable solvents are hydrocarbons such as benzene, toluene, xylenes or mesitylene; halogenated hydrocarbons such as dichloromethane, trichloroethylene or chlorobenzene; alcohols such as methanol, ethanol or isopropanol; glycols and glycol ethers such as ethylene glycol, diethylene glycol and 2-methoxyethanol; nitriles such as acetonitrile; ethers such as tetrahydrofuran or dioxane; amides such as dimethylformamide (DMF) and sulfoxides such as dimethyl sulfoxide. Mixtures of these solvents are also suitable.

It is also possible to prepare a compound of the formula I by reacting a compound of the formula IV in which $R^1$, $R^2$, $R^3$, $R^4$, Q and X possess the meanings already given with an amine of the formula V or VI.

Compounds of the formula IV can be prepared by alkylating thiadiazinones of the formula II in accordance with methods which are known per se and known to those skilled in the art, while the amines of the formulae V and VI are as a rule known compounds which are offered for sale commercially.

It is also possible to alkylate in a conventional manner a compound which corresponds to the formula I but which possesses, instead of $R^5$, a primary or secondary amino group.

It is likewise possible to react a compound which corresponds to the formula I but which contains, instead of $R^3$ and/or $R^4$, one or two free OH groups with a compound of the formula $R^3$-X or $R^4$-X in which $R^3$, $R^4$ and X have the meanings given. The etherification of the OH groups is performed by methods which are known per se, as described in standard works of the chemical literature (for example in Houben-Weyl, Methoden der Organischen Chemie [Methods of Organic Chemistry], Georg Thieme Verlag, Stuttgart or in Organic Reactions, John Wiley & Sons Inc., New York), specifically under the reaction conditions which are known and suitable for the stated reactions. In this context it is also possible to make use of variants which are known per se and which are not mentioned in more detail here.

A resulting base of the formula I can be converted into the corresponding acid addition salt using an acid. Suitable acids for this reaction are those which give physiologically acceptable salts. For instance, it is possible to use inorganic acids, for example sulfuric acid, hydrohalic acids such as hydrochloric acid or hydrobromic acid, phosphoric acids such as orthophosphoric acid, nitric acid, sulfamic acid, and also organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and disulfonic acids, and laurylsulfuric acid.

The free bases of the formula I can if desired be liberated from their salts by treatment with strong bases such as sodium hydroxide or potassium hydroxide, sodium carbonate or potassium carbonate.

Compounds of the formula I may contain one or more centers of asymmetry. In this case they are customarily present in racemic form. Racemates which are obtained can be separated into their optical antipodes by mechanical or chemical methods which are known per se. Preferably, diastereomers are formed from the racemic mixture by reaction with an optically active separating agent.

It is of course also possible to obtain optically active compounds of the formula I in accordance with the methods described above, by using starting substances which are already optically active. For example, it is possible to replace the compound mentioned in Example 1 at lines 11 and 12 by 5-(3,4-dimethoxyphenyl)-6-(S)-ethyl-3,6-dihydro-1,3,4-thiadiazin-2-one or its (R)-enantiomer.

The invention further relates to the use of the compounds of the formula I and their physiologically acceptable salts for the preparation of pharmaceutical formulations, in particular by a non-chemical route. In this context they can be brought into a suitable dosage form together with at least one solid, liquid and/or semi-liquid excipient or auxiliary and, if appropriate, in combination with one or more further active substances.

The invention furthermore relates to agents, in particular pharmaceutical formulations, containing at least one compound of the formula I and/or one of its physiologically acceptable salts.

These formulations can be used as medicaments in human or veterinary medicines. Possible excipients are organic or inorganic substances which are suitable for enteral (for example oral), parenteral or topical administration and which do not react with the novel compounds, for example water, vegetable oils, benzyl alcohols, polyethylene glycols, glycerol triacetate, gelatin, carbohydrates such as lactose or starch, magnesium stearate, talc or petroleum jelly. Tablets, coated tablets, capsules, syrups, elixirs or drops are used, in particular, for oral administration, suppositories are used for rectal administration, solutions—preferably oily or aqueous solutions—and furthermore suspensions, emulsions or implants are used for parenteral administration, and ointments, creams or powders are used for topical application. The novel compounds can also be lyophilized and the lyophilizates obtained can be used, for example, for the production of injection preparations. The formulations indicated can be sterilized and/or can contain auxiliaries such as lubricants, preservatives, stabilizers and/or wetting agents, emulsifiers, salts for influencing the osmotic pressure, buffer substances, colouring substances, flavouring substances and/or aroma substances. If desired they may also contain one or more further active substances, for example one or more vitamins.

The compounds of the formula I can be used in combating diseases, in particular asthmatic disorders and cardiac insufficiency, and in the therapeutic treatment of the human or animal body.

In this context, the substances according to the invention are generally administered in analogy to known, positively inotropically active substances, for example, Amrinon ® or 5-amino-[3,4-bipyridine]-6(1H)-one, or antiasthmatics, for example, Atrovent ® or 8-azoniabicyclo[3.2.1]octane, 3-(3-hydroxy-1-oxo-2-phenylpropoxy)-8-methyl-8-(1-methylethyl)bromide, monohydrate (endo,syn)±, preferably in doses of between 1 and 100 mg, in particular between 2 and 20 mg per dosage unit. The daily dosage is preferably between about 0.2 and 2 mg/kg of body weight. The substances according to the present invention are useful for all other purposes in the recited dosage ranges. However, the specific dose for each particular patient depends on a great variety of factors, for example on the activity of the specific compound employed, on the age, body weight, general state of health, sex, on the diet, on the time of and route of administration and on the rate of excretion, medicament combination and severity of the particular disease to which the therapy is applied. Oral administration is preferred. In contrast to the digitalis glycosides hitherto used for the therapy of cardiac insufficiency, the compounds of the formula I are distinguished by improved therapeutic scope and peripheral relief.

In the following examples "customary work-up" denotes:

Water or dilute sodium hydroxide solution is added if necessary, the mixture is extracted with an organic solvent such as ethyl acetate, chloroform or dichloromethane, the phases are separated, the organic phase is dried over sodium sulfate, filtered and evaporated, and the residue is purified by chromatography and/or crystallization.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosures of all applications, patents, and publications cited herein, and of corresponding German P 43 10 699.4, filed Apr. 1, 1993, are hereby incorporated by reference.

EXAMPLE 1

0.6 g of potassium tert-butylate is added to a solution of 1.5 g of 5-(3,4-dimethoxyphenyl)-6-ethyl-3,6-dihydro-1,3,4-thiadiazin-2-one [obtainable by reacting 1-(3,4-dimethoxyphenyl)-2-bromobutan-1-one with methyl hydrazinethioformate] in 30 ml of dimethylformamide (DMF), and the mixture is stirred for 30 minutes. A solution of 3-chloropropyldimethylamine in toluene is then added and the mixture is boiled for three hours. The solvent is removed in vacuo, and the mixture is worked up as usual to give 3-dimethylaminopropyl-5-(3,4-dimethoxyphenyl)-6-ethyl-3,6-dihydro-1,3,4-thiadiazin-2-one, m.p. 175° (hydrochloride).

The following compounds are obtained analogously by reacting 3-chloropropyldimethylamine with 5-(3-methoxy-4-trifluoromethoxyphenyl)-6-ethyl-3,6-dihydro-1,3,4-thiadiazin-2-one:
   3-dimethylaminopropyl-5-(3-methoxy-4-trifluoromethoxyphenyl)-6-ethyl-3,6-dihydro-1,3,4-thiadiazin-2-one;
with 5-(3-methoxy-4-difluoromethoxyphenyl)-6-ethyl-3,6-dihydro-1,3,4-thiadiazin-2-one:
   3-dimethylaminopropyl-5-(3-methoxy-4-difluoromethoxyphenyl)-6-ethyl-3,6-dihydro-1,3,4-thiadiazin-2-one;
with 5-(3-methoxy-4-fluoromethoxyphenyl)-6-ethyl-3,6-dihydro-1,3,4-thiadiazin-2-one:
   3-dimethylaminopropyl-5-(3-methoxy-4-fluoromethoxyphenyl)-6-ethyl-3,6-dihydro-1,3,4-thiadiazin-2-one;
with 5-(3-difluoromethoxy-4-methoxyphenyl)-6-ethyl-3,6-dihydro-1,3,4-thiadiazin-2-one:
   3-dimethylaminopropyl-5-(3-difluoromethoxy-4-methoxyphenyl)-6-ethyl-3,6-dihydro-1,3,4-thiadiazin-2-one, m.p. 139° (fumarate);
with 5-[3-(2,2,2-trifluoroethoxy)-4-methoxyphenyl]-6-ethyl-3,6-dihydro-1,3,4-thiadiazin-2-one:
   2-dimethylaminoethyl-5-[3-(2,2,2-trifluoroethoxy)-4-methoxyphenyl]-6-ethyl-3,6-dihydro-1,3,4-thiadiazin-2-one, m.p. 155° (fumarate);
with 5-(3-fluoromethoxy-4-methoxyphenyl)-6-ethyl-3,6-dihydro-1,3,4-thiadiazin-2-one:
   3-dimethylaminopropyl-5-(3-fluoromethoxy-4-methoxyphenyl)-6-ethyl-3,6-dihydro-1,3,4-thiadiazin-2-one;
with 5-(3-methoxy-4-ethoxyphenyl)-6-ethyl-3,6-dihydro-1,3,4-thiadiazin-2-one:
   3-dimethylaminopropyl-5-(3-methoxy-4-ethoxyphenyl)-6-ethyl-3,6-dihydro-1,3,4-thiadiazin-2-one, m.p. 102° (fumarate);
with 5-(3-ethoxy-4-methoxyphenyl)-6-ethyl-3,6-dihydro-1,3,4-thiadiazin-2-one:
   3-dimethylaminopropyl-5-(3-ethoxy-4-methoxyphenyl)-6-ethyl-3,6-dihydro-1,3,4-thiadiazin-2-one, m.p. 181° (fumarate);
with 5-(3-methoxy-4-hydroxyphenyl)-6-ethyl-3,6-dihydro-1,3,4-thiadiazin-2-one:
   3-dimethylaminopropyl-5-(3-methoxy-4-hydroxyphenyl)-6-ethyl-3,6-dihydro-1,3,4-thiadiazin-2-one.

EXAMPLE 2

In analogy to Example 1, by reacting 5-(3,4-dimethoxyphenyl)-3,6-dihydro-1,3,4-thiadiazin-2-one with 3-chloropropyldimethylamine, 3-dimethylaminopropyl-5(3,4-dimethoxyphenyl)-3,6-dihydro-1,3,4-thiadiazin-2-one is obtained; m.p. 195°.

The following compounds are obtained analogously by reacting 2-chloroethyldimethylamine with 5-(3,4dimethoxyphenyl)-6-ethyl-3,6-dihydro-1,3,4-thiadiazin-2-one:
   2-dimethylaminoethyl-5-(3,4-dimethoxyphenyl)-6-ethyl-3,6-dihydro-1,3,4-thiadiazin-2-one;
with 5-(3-methoxy-4-trifluoromethoxyphenyl)-6-ethyl-3,6-dihydro-1,3,4-thiadiazin-2-one:
   2-dimethylaminoethyl-5-(3-methoxy-4-trifluoromethoxyphenyl)-6-ethyl-3,6-dihydro-1,3,4-thiadiazin-2-one;
with 5-(3-methoxy-4-difluoromethoxyphenyl)-6-ethyl-3,6-dihydro-1,3,4-thiadiazin-2-one:
   2-dimethylaminoethyl-5-(3-methoxy-4-difluoromethoxyphenyl)-6-ethyl-3,6-dihydro-1,3,4-thiadiazin-2-one;
with 5-(3-methoxy-4-fluoromethoxyphenyl)-6-ethyl-3,6-dihydro-1,3,4-thiadiazin-2-one:
   2-dimethylaminoethyl-5-(3-methoxy-4-fluoromethoxyphenyl)-6-ethyl-3,6-dihydro-1,3,4-thiadiazin-2-one;
with 5-(3-difluoromethoxy-4-methoxyphenyl)-6-ethyl-3,6-dihydro-1,3,4-thiadiazin-2-one:

2-dimethylaminoethyl-5-(3-difluoromethoxy-4-methoxyphenyl)-6-ethyl-3,6-dihydro-1,3,4-thiadiazin-2-one;
with 5-(3-fluoromethoxy-4-methoxyphenyl)-6-ethyl-3,6-dihydro-1,3,4-thiadiazin-2-one:
2-dimethylaminoethyl-5-(3-fluoromethoxy-4-methoxyphenyl)-6-ethyl-3,6-dihydro-1,3,4- thiadiazin-2-one;
with 5-(3-methoxy-4-ethoxyphenyl)-6-ethyl-3,6-dihydro-1,3,4-thiadiazin-2-one:
2-dimethylaminoethyl-5-(3-methoxy-4-ethoxyphenyl)-6-ethyl-3,6-dihydro-1,3,4-thiadiazin-2-one;
with 5-(3-ethoxy-4-methoxyphenyl)-6-ethyl-3,6-dihydro-1,3,4-thiadiazin-2-one:
2-dimethylaminoethyl-5-(3-ethoxy-4-methoxyphenyl)-6-ethyl-3,6-dihydro-1,3,4-thiadiazin-2-one;
with 5-(3-hydroxy-4-methoxyphenyl)-6-ethyl-3,6-dihydro-1,3,4-thiadiazin-2-one:
2-dimethylaminoethyl-5-(3-hydroxy-4-methoxyphenyl)-6-ethyl-3,6-dihydro-1,3,4-thiadiazin-2-one.

EXAMPLE 3

After the addition of one equivalent of 3-iodo-1,1,2,2,3-pentafluoropropane to a solution of 2.3 g of 3-morpholinopropyl-5-(3-methoxy-4-hydroxyphenyl)-6-ethyl-3,6-dihydro-1,3,4-thiadiazin-2-one [obtainable by reacting 1-(4-hydroxy-3-methoxyphenyl)-2-bromobutan-1-one with methyl hydrazinethioformate followed by reaction with 1-chloro-3-morpholinopropane] in THF, the mixture is boiled for two hours. The solvent is then removed in vacuo and the mixture is worked up as usual. 3-Morpholinopropyl-5-[3-methoxy-4-(1,1,2,2,3-pentafluoropropoxyphenyl)]-6-ethyl-3,6-dihydro-1,3,4-thiadiazin-2-one is obtained.

The following compounds are obtained analogously by etherifying the corresponding mono- or dihydroxyphenyl-1,3,4-thiadiazinone derivatives with polyfluoroalkyl halides:
3-dimethylaminopropyl-5-(3-methoxy-4-trifluoromethoxyphenyl)-3,6-dihydro-1,3,4-thiadiazin-2-one;
3-dimethylaminopropyl-5-(4-trifluoromethoxyphenyl)-3,6-dihydro-1,3,4-thiadiazin-2-one;
3-dimethylaminopropyl-5-[3,4-bis (difluoromethoxy)-phenyl]-3,6-dihydro-1,3,4-thiadiazin -2-one;
3-dimethylaminopropyl-5-[3-methoxy-4-(1,1,2-trifluoroethoxy)phenyl]-3,6-dihydro-1,3,4-thiadiazin-2-one;
3-dimethylaminopropyl-5-[3,4-bis(chloromethoxy)-phenyl]-3,6-dihydro-1,3,4 -thiadiazin-2-one.

EXAMPLE 4

In analogy to Example 1, by reacting 5-(3-methoxy-4-fluoromethoxyphenyl)-6-ethyl-3,6-dihydro-1,3,4thiadiazin-2-one with 1-chloro-3-morpholinopropane, 3-morpholinopropyl-5-(3-methoxy-4-fluoromethoxyphenyl)-6-ethyl-3,6-dihydro-1,3,4-thiadiazin-2-one is obtained.

The following compounds are obtained analogously by reaction
of: 5-(3-methoxy-4-trifluoromethoxyphenyl)-6-ethyl-3,6-dihydro-1,3,4-thiadiazin-2-one with 1-chloro-3-morpholinopropane:
3-morpholinopropyl-5-(3-methoxy-4-trifluoromethoxyphenyl)-6-ethyl-3,6-dihydro-1,3,4-thiadiazin-2-one;
of 5-(3-methoxy-4-difluoromethoxyphenyl)-6-ethyl-3,6-dihydro-1,3,4-thiadiazin-2-one with 1-chloro-3-piperidinopropane:
3-piperidinopropyl-5-(3-methoxy-4-difluoromethoxyphenyl)-6-ethyl-3,6-dihydro-1,3,4-thiadiazin-2-one;
of 5-(3,4-dimethoxyphenyl)-6-ethyl-3,6-dihydro-1,3,4-thiadiazin-2-one with 1-chloro-3-morpholinopropane:
3-morpholinopropyl-5-(3,4-dimethoxyphenyl)-6-ethyl-3,6-dihydro-1,3,4-thiadiazin-2-one, m.p. 136° (oxalate);
of 5-(3,4-dimethoxyphenyl)-6-ethyl-3,6-dihydro-1,3,4-thiadiazin-2-one with 1-chloro-3-piperidinopropane:
3-piperidinopropyl-5-(3,4-dimethoxyphenyl)-6-ethyl-3,6-dihydro-1,3,4-thiadiazin-2-one, m.p. 121°, (oxalate);
of 5-(3,4-dimethoxyphenyl)-6-ethyl-3,6-dihydro-1,3,4-thiadiazin-2-one with 1-chloro-3-pyrrolidinopropane:
3-pyrrolidinopropyl-5-(3,4-dimethoxyphenyl)-6-ethyl-3,6-dihydro-1,3,4-thiadiazin-2-one;
of 5-(3-methoxy-4-ethoxyphenyl)-6-ethyl-3,6-dihydro-1,3,4-thiadiazin-2-one with 1-chloro-3-morpholinopropane:
3-morpholinopropyl-5-(3-methoxy-4-ethoxyphenyl)-6-ethyl-3,6-dihydro-1,3,4-thiadiazin-2-one, m.p. 157° (fumarate);
of 5-(3-methoxy-4-ethoxyphenyl)-6-ethyl-3,6-dihydro-1,3,4-thiadiazin-2-one with 1-chloro-3-piperidinopropane:
3-piperidinopropyl-5-(3-methoxy-4-ethoxyphenyl)-6-ethyl-3,6-dihydro-1,3,4-thiadiazin-2-one, m.p. 134° (fumarate);
of 5-(3-methoxy-4-ethoxyphenyl)-6-ethyl-3,6-dihydro-1,3,4-thiadiazin-2-one with 1-chloro-3-pyrrolidinopropane:
3-pyrrolidinopropyl-5-(3-methoxy-4-ethoxyphenyl)-6-ethyl-3,6-dihydro-1,3,4-thiadiazin-2-one;
of 5-(3-ethoxy-4-methoxyphenyl)-6-ethyl-3,6-dihydro-1,3,4-thiadiazin-2-one with 1-chloro3-morpholinopropane:
3-morpholinopropyl-5-(3-ethoxy-4-methoxyphenyl)-6-ethyl-3,6-dihydro-1,3,4-thiadiazin-2-one, m.p. 190° (fumarate);
of 5-(3-ethoxy-4-methoxyphenyl)-6-ethyl-3,6-dihydro-1,3,4-thiadiazin-2-one with 1-chloro-3-piperidinopropane:
3-piperidinopropyl-5-(3-ethoxy-4-methoxyphenyl)-6-ethyl-3,6-dihydro-1,3,4-thiadiazin-2-one, m.p. 165° (fumarate);
of 5-(3-methoxy-4-difluoromethoxyphenyl)-6-ethyl-3,6-dihydro-1,3,4-thiadiazin-2-one with 1-chloro-3-morpholinopropane:
3-morpholinopropyl-5-(3-methoxy-4-difluoromethoxyphenyl)-6-ethyl-3,6-dihydro-1,3,4-thiadiazin-2-one, m.p. 118° (fumarate);
of 5-(3-difluoromethoxy-4-methoxyphenyl)-6-ethyl-3,6-dihydro-1,3,4-thiadiazin-2-one with 1-chloro-3-piperidinopropane:
3-piperidinopropyl-5-(3-difluoromethoxy-4-methoxyphenyl)-6-ethyl-3,6-dihydro-1,3,4-thiadiazin-2-one, m.p. 104 ° (hydrochloride);
of 5-(3-methoxy-4-difluoromethoxyphenyl)-6-ethyl-3,6-dihydro-1,3,4-thiadiazin-2-one with 1-chloro-3-pyrrolidinopropane:
3-pyrrolidinopropyl-5-(3-methoxy-4-difluoromethoxyphenyl)-6-ethyl-3,6-dihydro-1,3,4-thiadiazin-2-one;
of 5-(3-methoxy-4-fluoromethoxyphenyl)-6-ethyl-3,6-dihydro-1,3,4-thiadiazin-2-one with 1-chloro-3-morpholinopropane:
3-morpholinopropyl-5-(3-methoxy-4-fluoromethoxyphenyl)-6-ethyl-3,6-dihydro-1,3,4-thiadiazin-2-one;

of 5-(3-methoxy-4-fluoromethoxyphenyl)-6-ethyl-3,6-dihydro-1,3,4-thiadiazin-2-one with 1-chloro-3-piperidinopropane:

3-piperidinopropyl-5-(3-methoxy-4-fluoromethoxyphenyl)-6-ethyl-3,6-dihydro-1,3,4-thiadiazin-2-one;

of 5-(3-methoxy-4-fluoromethoxyphenyl)-6-ethyl-3,6-dihydro-1,3,4-thiadiazin-2-one with 1-chloro-3-pyrrolidinopropane:

3-pyrrolidinopropyl-5-(3-methoxy-4-fluoromethoxyphenyl)-6-ethyl-3,6-dihydro-1,3,4-thiadiazin-2-one;

of 5-(3-methoxy-4-difluoromethoxyphenyl)-6-ethyl-3,6-dihydro-1,3,4-thiadiazin-2-one with 1-chloro-3-morpholinopropane:

3-morpholinopropyl-5-(3-methoxy-4-difluoromethoxyphenyl)-6-ethyl-3,6-dihydro-1,3,4-thiadiazin-2-one;

of 5-(3-methoxy-4-difluoromethoxyphenyl)-6-ethyl-3,6-dihydro-1,3,4-thiadiazin-2-one with 1-chloro-3-piperidinopropane:

3-piperidinopropyl-5-(3-methoxy-4-difluoromethoxyphenyl)-6-ethyl-3,6-dihydro-1,3,4-thiadiazin-2-one;

of 5-(3-methoxy-4-difluoromethoxyphenyl)-6-ethyl-3,6-dihydro-1,3,4-thiadiazin-2-one with 1-chloro-3-pyrrolidinopropane:

3-pyrrolidinopropyl-5-(3-methoxy-4-difluoromethoxyphenyl)-6-ethyl-3,6-dihydro-1,3,4-thiadiazin-2-one;

of 5-[3-(2,2,2-trifluoroethoxy)-4-methoxyphenyl]-6-ethyl-3,6-dihydro-1,3,4-thiadiazin-2-one with 1-chloro-3-piperidinopropane:

3-piperidinopropyl-5-[3-(2,2,2-trifluoroethoxy)-4-methoxyphenyl]-6-ethyl-3,6-dihydro-1,3,4-thiadiazin-2-one, m.p. 142° (fumarate);

of 5-[3-(2,2,2-trifluoroethoxy)-4-methoxyphenyl]-6-ethyl-3,6-dihydro-1,3,4-thiadiazin-2-one with 1-chloro-3-morpholinopropane:

3-morpholinopropyl-5-[3-(2,2,2-trifluoroethoxy)-4-methoxyphenyl]-6-ethyl-3,6-dihydro-1,3,4-thiadiazin-2-one, m.p. 162° (fumarate).

EXAMPLE 5

In analogy to Example 4, by reacting 5-(3-methoxy-4-fluoromethoxyphenyl)-6-ethyl-3,6-dihydro-1,3,4-thiadiazin-2-one with 1-chloro-2-morpholinoethane, 2-morpholinoethyl-5-(3-methoxy-4-fluoromethoxyphenyl)-6-ethyl-3,6-dihydro-1,3,4-thiadiazin-2-one is obtained.

The following compounds are obtained analogously by reaction of 5-(3-methoxy-4-trifluoromethoxyphenyl)-6-ethyl-3,6-dihydro-1,3,4-thiadiazin-2-one with 1-chloro-2-morpholinoethane:

2-morpholinoethyl-5-(3-methoxy-4-trifluoromethoxyphenyl)-6-ethyl-3,6-dihydro-1,3,4-thiadiazin-2-one;

of 5-(3-methoxy-4-difluoromethoxyphenyl)-6-ethyl-3,6-dihydro-1,3,4-thiadiazin-2-one with 1-chloro-2-piperidinoethane:

2-piperidinoethyl-5-(3-methoxy-4-difluoromethoxyphenyl)6-ethyl-3,6-dihydro-1,3,4-thiadiazine-2-one;

of 5-(3,4-dimethoxyphenyl)-6-ethyl-3,6-dihydro-1,3,4-thiadiazin-2-one with 1-chloro-2-morpholinoethane:

2-morpholinoethyl-5-(3,4-dimethoxyphenyl)-6-ethyl-3,6-dihydro-1,3,4-thiadiazin-2-one;

of 5-(3,4-dimethoxyphenyl)-6-ethyl-3,6-dihydro-1,3,4-thiadiazin-2-one with 1-chloro-2-piperidinoethane:

2-piperidinoethyl-5-(3,4-dimethoxyphenyl)-6-ethyl-3,6-dihydro-1,3,4-thiadiazin-2-one;

of 5-(3,4-dimethoxyphenyl)-6-ethyl-3,6-dihydro-1,3,4-thiadiazin-2-one with 1-chloro-2-pyrrolidinoethane:

2-pyrrolidinoethyl-5-(3,4-dimethoxyphenyl)-6-ethyl-3,6-dihydro-1,3,4-thiadiazin-2-one;

of 5-(3-methoxy-4-ethoxyphenyl)-6-ethyl-3,6-dihydro-1,3,4-thiadiazin-2-one with 1-chloro-2-morpholinoethane:

2-morpholinoethyl-5-(3-methoxy-4-ethoxyphenyl)-6-ethyl-3,6-dihydro-1,3,4-thiadiazin-2-one;

of 5-(3-methoxy-4-ethoxyphenyl)-6-ethyl-3,6-dihydro-1,3,4-thiadiazin-2-one with 1-chloro-2-piperidinoethane:

2-piperidinoethyl-5-(3-methoxy-4-ethoxyphenyl)-6-ethyl-3,6-dihydro-1,3,4-thiadiazin-2-one;

of 5-(3-methoxy-4-ethoxyphenyl)-6-ethyl-3,6-dihydro-1,3,4-thiadiazin-2-one with 1-chloro-2-pyrrolidinoethane;

2-pyrrolidinoethyl-5-(3-methoxy-4-ethoxyphenyl)-6-ethyl-3,6-dihydro-1,3,4-thiadiazin-2-one;

of 5-(3-methoxy-4-difluoromethoxyphenyl)-6-ethyl-3,6-dihydro-1,3,4-thiadiazin-2-one with 1-chloro-2-morpholinoethane:

2-morpholinoethyl-5-(3-methoxy-4-difluoromethoxyphenyl)-6-ethyl-3,6-dihydro-1,3,4-thiadiaz-2-one;

of 5-(3-methoxy-4-difluoromethoxyphenyl)-6-ethyl-3,6-dihydro-1,3,4-thiadiazin-2-one with 1-chloro-2-piperidinoethane:

2-piperidinoethyl-5-(3-methoxy-4-difluoromethoxyphenyl)-6-ethyl-3,6-dihydro-1,3,4-thiadiazin-2-one;

of 5-(3-methoxy-4-difluoromethoxyphenyl)-6-ethyl-3,6-dihydro-1,3,4-thiadiazin-2-one with 1-chloro-2-pyrrolidinoethane:

2-pyrrolidinoethyl-5-(3-methoxy-4-difluoromethoxyphenyl)-6-ethyl-3,6-dihydro-1,3,4-thiadiazin-2-one;

of 5-(3-methoxy-4-fluoromethoxyphenyl)-6-ethyl-3,6-dihydro-1,3,4-thiadiazin-2-one with 1-chloro-2-pyrrolidinoethane:

2-morpholinoethyl-5-(3-methoxy-4-fluoromethoxyphenyl)-6-ethyl-3,6-dihydro-1,3,4-thiadiazin-2-one:

of 5-(3-methoxy-4-fluoromethoxyphenyl)-6-ethyl-3,6-dihydro-1,3,4-thiadiazin-2-one with 1-chloro-2-piperidinoethane:

2-piperidinoethyl-5-(3-methoxy-4-fluoromethoxyphenyl)-6-ethyl-3,6-dihydro-1,3,4-thiadiazin-2-one;

of 5-(3-methoxy-4-fluoromethoxyphenyl)-6-ethyl-3,6-dihydro-1,3,4-thiadiazin-2-one with 1-chloro-2-pyrrolidinoethane:

2-pyrrolidinoethyl-5-(3-methoxy-4-fluoromethoxyphenyl)-6-ethyl-3,6-dihydro-1,3,4-thiadiazin-2-one;

of 5-(3-methoxy-4-difluoromethoxyphenyl)-6-ethyl-3,6-dihydro-1,3,4-thiadiazin-2-one with 1-chloro-2-morpholinoethane:

2-morpholinoethyl-5-(3-methoxy-4-difluoromethoxyphenyl)-6-ethyl-3,6-dihydro-1,3,4-thiadiazin-2-one;

of 5-(3-methoxy-4-difluoromethoxyphenyl)-6-ethyl-3,6-dihydro-1,3,4-thiadiazin-2-one with 1-chloro-2-piperidinoethane:

2-piperidinoethyl-5-(3-methoxy-4-difluoromethoxyphenyl)-6-ethyl-3,6-dihydro-1,3,4-thiadiazin-2-one;

of 5-(3-methoxy-4-difluoromethoxyphenyl)-6-ethyl-3,6-dihydro-1,3,4-thiadiazin-2-one with 1-chloro-2-pyrrolidinoethane:

2-pyrrolidinoethyl-5-(3-methoxy-4-difluoromethoxyphenyl)-6-ethyl-3,6-dihydro-1,3,4-thiadiazin-2-one;

The following examples relate to pharmaceutical formulations.

Example A: Injection Bottles

A solution of 100 g of 3-dimethylaminopropyl-5-(3,4-dimethoxyphenyl)-6-ethyl-3,6-dihydro-1,3,4 -thiadiazinone and 5 g of disodium hydrogen phosphate in 3 l of double-distilled water is adjusted with 2N hydrochloric acid to a pH of 6.5, subjected to sterile filtration dispensed into injection bottles, lyophilized under sterile conditions and subjected to sterile sealing. Each injection bottle contains 5 mg of active substance Example B: Suppositories A mixture of 20 g of 3-dimethylaminopropyl -5-(3,4-dimethoxyphenyl)-3,6-dihydro-1,3,4-thiadiazin-2-one is melted with 100 g of soya lecithin and 1400 g of cocos butter, poured into moulds and allowed to cool. Each suppository contains 20 mg of active substance.

Example C: Solution

A solution is prepared from 1 g of 3-piperidinopropyl-5-(3-methoxy-4-difluoromethoxyphenyl)-6-ethyl -3,6-dihydro-1,3,4-thiadiazin-2-one, 9.38 g of $NaH_2PO_4 \times 2\ H_2O$, 28.4 8 g of $Na_2HPO_4 \times 12\ H_2O$ and 0.1 g of benzalkonium chloride in 940 ml of double-distilled water. The pH adjusted to 6.8, and the solution is made up to 1 l and sterilized by irradiation. This solution can be used the form of eyedrops.

Example D: Ointment 500 mg of 3-morpholinopropyl-5-(3-methoxy-4-difluoromethoxyphenyl)-6-ethyl-3,6-dihydro-1,3,4-thiadiazin-2-one are mixed with 99.5 g of petroleum jelly under aseptic conditions.

Example E: Tablets

A mixture of 1 kg of 3-pyrrolidinopropyl-5-(3-methoxy-4-fluoromethoxyphenyl)-6-ethyl-3,6-dihydro-1,3,4-thiadiazin-2-one, 4 kg of lactose, 1.2 kg of potato starch, 0.2 kg of talc and 0.1 kg of magnesium stearate is pressed to give tablets in a customary manner such that each tablet contains 10 mg of active substance.

Example F: Coated tablets

Tablets are pressed analogously to Example E and are subsequently coated in a customary manner with coating of sucrose, potato starch, talc, tragacanth and colouring substance.

Example G: Capsules 2 kg of 3-pyrrolidinopropyl-5-(3-methoxy-4-fluoromethoxyphenyl)-6-ethyl-3,6-dihydro-1,3,4-thiadiazin-2-one are dispensed into hard gelatin capsules in a conventional manner, so that each capsule contains 20 mg of active substance.

Example H: Ampoules

A solution of 1 kg of 3-pyrrolidinopropyl-5-(3-methoxy-4-fluoromethoxyphenyl)-6-ethyl-3,6-dihydro-1,3,4-thiadiazin-2-one in 60 l of double-distilled water is subjected to sterile filtration, dispensed into ampoules, lyophilized under sterile conditions and subjected to sterile sealing. Each ampoule contains 10 mg of active substance.

It is possible analogously to obtain all stated pharmaceutical formulations which contain one or more of the other active substances of the formula I and/or their physiologically acceptable acid addition salts.

The preceding examples can be repeated with similar success by substituting the generically or specifically described reactants and/or operating conditions of this invention for those used in the preceding examples From the foregoing description, one skilled in the art can easily ascertain the essential characteristics of this invention and, without departing from the spirit and scope thereof, can make various changes and modifications of the invention to adapt it to various usages and conditions.

We claim:

1. A thiadiazinone compound of the formula I

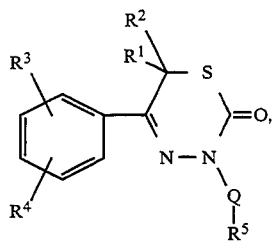

wherein
$R^1$ and $R^2$ are in each case independently of one another H or A,
$R^3$ and $R^4$ are in each case independently of one another —OH, —OA, —S—A, —SO—A, —SO$_2$—A, Hal, methylenedioxy, cycloalkyloxy having 3–7 carbon atoms or O—$C_mH_{2m+1-k}F_k$,
$R^5$ is —$NR^6R^7$ or

where one $CH_2$ group can also be replaced by oxygen,
$R^6$ and $R^7$ are in each case independently of one another H or A,
Q is alkylene having 1–6 carbon atoms,
A is alkyl having 1–6 carbon atoms,
Hal is F, Cl, Br or I,
m is 1, 2, 3, 4, 5 or 6,
n is 3, 4, 5 or 6
and
k is 1, 2, 3, 4, 5, 6, 7, 8, 9, 10, 11, 12 or 13, or a physiologically acceptable salt thereof.

2. A racemate of a compound of the formula I, according to claim 1.

3.
a) 3-Dimethylaminopropyl-5-(3,4 -dimethoxyphenyl)-6-ethyl-3,6-dihydro-1,3,4-thiadiazin-2-one;
b) 3-dimethylaminopropyl-5-(3,4-dimethoxyphenyl)-3,6-dihydro-1,3,4-thiadiazin-2-one;
c) 3-dimethylaminoethyl-5-(3,4-dimethoxyphenyl)-6-ethyl-3,6-dihydro-1,3,4-thiadiazin-2-one;
d) 3-piperidinopropyl-5-(3-methoxy-4-difluoromethoxyphenyl)-6-ethyl-3,6-dihydro-1,3,4thiadiazin-2-one;
e) 3-morpholinopropyl-5-(3-methoxy-4-difluoromethoxyphenyl)-6-ethyl-3,6-dihydro-1,3,4-thiadiazin-2-one.

4. A compound according to claim 1, wherein $R^3$ and $R^4$ are in the 3- and 4-positions of the phenyl ring, respectively; and $R^1$ is H, $R^2$ is H or alkyl, and $R^3$ is OA.

5. A compound according to claim 1, wherein $R^3$ and $R^4$ are in the 3- and 4-positions of the phenyl ring, respectively; and $R^1$ is H, $R^2$ is methyl or ethyl, and $R^3$ and $R^4$ are each OA.

6. A compound according to claim 1, wherein $R^3$ and $R^4$ are in the 3- and 4-positions of the phenyl ring, respectively; and $R^1$ is H, $R^2$ is methyl or ethyl, $R^3$ is OA, and $R^4$ is mono-, di-, or trifluoroalkoxy.

7. A compound according to claim 1, wherein $R^3$ and $R^4$ are in the 3- and 4-positions of the phenyl ring, respectively; and $R^1$ is H, $R^2$ is methyl or ethyl, $R^3$ is mono-, di-, or trifluoroalkoxy, and $R^4$ is OA.

8. A compound according to claim 1, wherein R3 and $R^4$ are in the 3- and 4-positions of the phenyl ring, respectively; and $R^1$ is H; $R^2$ is methyl or ethyl; $R^3$ and $R^4$ are, in each case independently of one another, OA or mono-, di-, or trifluoroalkoxy; and $R^5$-Q is 3-dimethylaminopropyl, 2-dimethylaminoethyl, 3-methylaminoproyl, 2-methylaminoethyl, 3-ethylaminopropyl, or 2-ethylaminoethyl.

9. A compound according to claim 1, wherein $R^3$ and $R^4$ are in the 3- and 4-positions of the phenyl ring, respectively; and $R^1$ is H; $R^2$ is methyl or ethyl; $R^3$ and $R^4$ are, in each case independently of one another, OA or mono-, di-, or trifluoroalkoxy; and $R^5$-Q is pyrrolidinoethyl, pyrrolidinopropyl, piperidinoethyl, piperidinopropyl, morpholinoethyl, or morpholinopropyl.

10. A pharmaceutical composition, comprising at least one compound of formula I according to claim 1 or a physiologically acceptable salt thereof and an excipient.

11. A method of inhibiting phosphodiesterase activity, comprising administering to a host in need thereof an effective amount of a compound according to claim 1.

12. A method of treating asthma or cardiac insufficiency, comprising administering to a host in need thereof an effective amount of a compound according to claim 1.

13. A method of treating allergy, inflammation, depression, or cardiovascular disorders, comprising administering to a host in need thereof an effective amount of a compound according to claim 1.

14. An isolated (R) or (S) enantiomer of a compound claim 2.

* * * * *